US012383244B2

(12) United States Patent
Wang

(10) Patent No.: US 12,383,244 B2
(45) Date of Patent: Aug. 12, 2025

(54) SPECIMEN RETRIEVAL BAG, SPECIMEN RETRIEVAL DEVICE AND METHOD FOR USING SPECIMEN RETRIEVAL DEVICE

(71) Applicant: SYSMFG (NANTONG) CO. LTD., Nantong (CN)

(72) Inventor: Haiying Wang, Nantong (CN)

(73) Assignee: VHMED (Nantong) Co. Ltd., Nantong (CN)

( * ) Notice: Subject to any disclaimer, the term of this patent is extended or adjusted under 35 U.S.C. 154(b) by 405 days.

(21) Appl. No.: 17/860,375

(22) Filed: Jul. 8, 2022

(65) Prior Publication Data

US 2023/0165574 A1 Jun. 1, 2023

Related U.S. Application Data

(63) Continuation of application No. PCT/CN2022/087395, filed on Apr. 18, 2022.

(30) Foreign Application Priority Data

Nov. 30, 2021 (CN) .......................... 202122980925.5

(51) Int. Cl.
*A61B 17/00* (2006.01)
*A61B 17/34* (2006.01)

(52) U.S. Cl.
CPC .... *A61B 17/00234* (2013.01); *A61B 17/3439* (2013.01); *A61B 2017/00287* (2013.01); *A61B 2017/00323* (2013.01)

(58) Field of Classification Search
CPC .......... A61B 17/00234; A61B 17/3439; A61B 2017/00287; A61B 2017/00323
See application file for complete search history.

(56) References Cited

U.S. PATENT DOCUMENTS 5,037,379 A 8/1991 Clayman et al.
5,074,867 A 12/1991 Wilk
(Continued)

FOREIGN PATENT DOCUMENTS

CN 201234972 Y 5/2009
CN 102188264 A 9/2011
(Continued)

OTHER PUBLICATIONS

Anonymity, How many types of disposable specimen collection bags are there? Published on http://www.homeportmedical.com/blog/24186.html, dated Aug. 19, 2019, retrieved on Nov. 14, 2022.
(Continued)

*Primary Examiner* — Tan-Uyen T Ho
*Assistant Examiner* — Cherie M Poland
(74) *Attorney, Agent, or Firm* — Westbridge IP LLC

(57) ABSTRACT

Disclosed is a specimen retrieval bag, which includes an introducing tab arranged at an opening end of the bag body; and a bag extending tab arranged on a closed end of the bag body; the introducing tab and the bag extending tab are configured to cooperate with an insertion rod, and the insertion rod is configured to pass through the bag extending tab to insert a top end of the insertion rod into the introducing tab. The beneficial effects of the present application are as follows: the diameter of the insertion rod may be effectively reduced, through using the specimen retrieval bag together with the insertion rod matching with the specimen retrieval bag, and a trocar cannula used in conjunction with the insertion rod is also reduced, thereby achieving an effect of minimally invasive in the true sense.

18 Claims, 13 Drawing Sheets

(56) References Cited

U.S. PATENT DOCUMENTS

| | | | |
|---|---|---|---|
| 5,190,555 A | 3/1993 | Wetter et al. | |
| 5,192,284 A | 3/1993 | Pleatman | |
| 5,785,677 A | 7/1998 | Auweiler | |
| 6,383,197 B1* | 5/2002 | Conlon | A61B 17/00234 606/127 |
| 6,409,733 B1* | 6/2002 | Conlon | A61B 17/00234 606/127 |
| 6,863,675 B2 | 3/2005 | Wilson, Jr. | |
| 8,075,567 B2 | 12/2011 | Taylor et al. | |
| 8,870,894 B2 | 10/2014 | Taylor et al. | |
| 9,414,817 B2 | 8/2016 | Taylor et al. | |
| 10,265,079 B2 | 4/2019 | Brodaczewski et al. | |
| 10,653,400 B2 | 5/2020 | Kamaraj et al. | |
| 2007/0088370 A1 | 4/2007 | Kahle et al. | |
| 2008/0234696 A1* | 9/2008 | Taylor | A61B 17/00234 606/114 |
| 2008/0312496 A1 | 12/2008 | Zwolinski | |
| 2011/0184431 A1* | 7/2011 | Parihar | A61B 17/00 606/114 |
| 2011/0190780 A1 | 8/2011 | O'Prey et al. | |
| 2016/0262739 A1 | 9/2016 | O'Prey et al. | |
| 2016/0324515 A1* | 11/2016 | Ravikumar | A61B 17/3468 |
| 2017/0128088 A1 | 5/2017 | Kahle et al. | |
| 2018/0221007 A1 | 8/2018 | Taylor et al. | |

FOREIGN PATENT DOCUMENTS

| | | |
|---|---|---|
| CN | 103892892 A | 7/2014 |
| CN | 104224242 A | 12/2014 |
| CN | 104368080 A | 2/2015 |
| CN | 104771222 A | 7/2015 |
| CN | 106618747 A | 5/2017 |
| CN | 107374711 A | 11/2017 |
| CN | 108543201 A | 9/2018 |
| CN | 108606814 A | 10/2018 |
| CN | 110547833 A | 12/2019 |
| CN | 212755738 U | 3/2021 |
| JP | H07328013 A | 12/1995 |
| JP | H08103501 A | 4/1996 |
| KR | 101739225 B1 | 5/2017 |

OTHER PUBLICATIONS

International Search Report issued in PCT Application No. PCT/CN2020/111109, dated Mar. 26, 2021.

* cited by examiner

SPECIMEN RETRIEVAL BAG, SPECIMEN RETRIEVAL DEVICE AND METHOD FOR USING SPECIMEN RETRIEVAL DEVICE

CROSS-REFERENCE TO RELATED APPLICATIONS

This application is a continuation of International Application No. PCT/CN2022/087395, filed on Apr. 18, 2022, which claims priority to Chinese Patent Application No. 202122980925.5, filed on Nov. 30, 2021. All of the aforementioned patent applications are hereby incorporated by reference in their entireties.

TECHNICAL FIELD

The present application relates to the technical field of medical devices, and more particularly, relates to a specimen retrieval bag, a specimen retrieval device, and a method for using the specimen retrieval device.

BACKGROUND

A trocar cannula is required in endoscopic surgery to facilitate an access of instruments and retrieval bags into and out of patient's body cavity. In order to achieve a purpose of minimally invasive, it is necessary to place a specimen retrieval bag with the largest possible capacity into the patient's body by using a trocar cannula with the smallest possible diameter.

At present, there are generally two types of specimen retrieval bags used in endoscopic surgery: one is a specimen retrieval bag with an operating rod, and the other is a specimen retrieval bag without an operating rod. The working diameter of the specimen retrieval bag with an operating rod is limited by an outer diameter of the operating rod, and an inner diameter of the trocar cannula required to be used must be larger than the outer diameter of the operating rod. For the convenience of operation, for the specimen retrieval bag without an operating rod, it is required to use an insertion cannula, the specimen retrieval bag is stored in the insertion cannula, and then the insertion cannula is inserted into the trocar cannula to enter and exit the patient's cavity. It can be seen that when the specimen retrieval bag without an operating rod is used, a trocar cannula with larger inner diameter is also needed.

SUMMARY

In order to solve the problem that the existing specimen retrieval bag needs to be used with a larger inner diameter trocar cannula, the purpose of the present application is to provide a specimen retrieval bag, a specimen retrieval device, and a method for using a specimen retrieval device.

In a first aspect, the present application provides a specimen retrieval bag, including: a bag body, an introducing tab arranged at an opening end of the bag body, and a bag extending tab arranged on a closed end of the bag body. The introducing tab and the bag extending tab are configured to cooperate with an insertion rod, and the insertion rod is configured to pass through the bag extending tab to insert a top end of the insertion rod into the introducing tab.

As further improvement of the present application, the specimen retrieval bag further includes a closure drawstring, the closure drawstring includes a closing section and an operating section that are connected to each other, the closing section is fixed to the opening end of the bag body through a pull ring, and the operating section passes through a trocar cannula and an end portion of the operating section is outside the trocar cannula.

As further improvement of the present application, the introducing tab and the bag extending tab are both provided with an X-ray developing belt.

As further improvement of the present application, the introducing tab is a cone.

In a second aspect, the present application provides a specimen retrieval device, including an insertion rod and the specimen retrieval bag according to the first aspect; the insertion rod and the specimen retrieval bag are separately designed, and the insertion rod is configured to pass through the bag extending tab to insert a top end of the insertion rod into the introducing tab.

As further improvement of the present application, the introducing tab is configured to be matched with a top end of the insertion rod.

As further improvement of the present application, an end of the insertion rod is set to be tapered.

As further improvement of the present application, the insertion rod is made of metal or hard fiber.

As further improvement of the present application, the insertion rod and the bag body are sealed in a packaging bag.

As further improvement of the present application, a length of the insertion rod is greater than that of the bag body.

As further improvement of the present application, an outer diameter of the insertion rod ranges from 1 millimeter to 3 millimeters.

In a third aspect, the present application provides a method for using a specimen retrieval device. The specimen retrieval device includes an insertion rod and a specimen retrieval bag, and the insertion rod and a specimen retrieval bag are separately designed. The specimen retrieval bag includes an introducing tab arranged at an opening end of the specimen retrieval bag, and a bag extending tab arranged on a closed end of the specimen retrieval bag. The method includes: inserting the specimen retrieval bag into a trocar cannula, and the insertion rod is configured to pass through the bag extending tab to insert a top end of the insertion rod into the introducing tab so that the specimen retrieval bag enters the trocar cannula; unfolding an opening end of the bag body, and placing a specimen into the specimen retrieval bag; and tightening the opening end of the specimen retrieval bag, and taking out the specimen retrieval bag As further improvement of the present application, the specimen retrieval bag further includes a closure drawstring, the closure drawstring includes a closing section and an operating section that are connected to each other, the closing section is fixed to the opening end of the specimen retrieval bag through a pull ring, and the operating section passes through a trocar cannula and an end portion of the operating section is outside the trocar cannula; the unfolding an opening end of the specimen retrieval bag includes: loosening the closure drawstring so that the opening end of the specimen retrieval bag is opened; and the tightening the opening end of the specimen retrieval bag includes: tightening the closure drawstring to tighten the opening end of the specimen retrieval bag.

As further improvement of the present application, before the inserting the specimen retrieval bag into a trocar cannula, the method further includes folding the specimen retrieval bag into a triangular shape to reduce a resistance of specimen retrieval bag when enters the trocar cannula.

The beneficial effects of the present application are as follows: a specimen retrieval bag and an insertion rod are separately designed, a diameter of the insertion rod may be effectively reduced, through using the specimen retrieval bag together with an insertion rod matching with the specimen retrieval bag, and a diameter of a trocar cannula used in conjunction with the insertion rod is also reduced, thereby achieving an effect of minimally invasive in the true sense.

BRIEF DESCRIPTION OF THE DRAWINGS

In order to illustrate the embodiments of the present application or the technical solutions in the prior art more clearly, the following will briefly introduce the accompanying drawings that are required to be used in the description of the embodiments or the prior art. Obviously, the accompanying drawings in the following description are only some embodiments of the present application, and for those of ordinary skill in the art, other drawings can also be obtained in accordance with these accompanying drawings without making any creative effort.

DETAILED DESCRIPTION OF THE EMBODIMENTS

Figure 1:
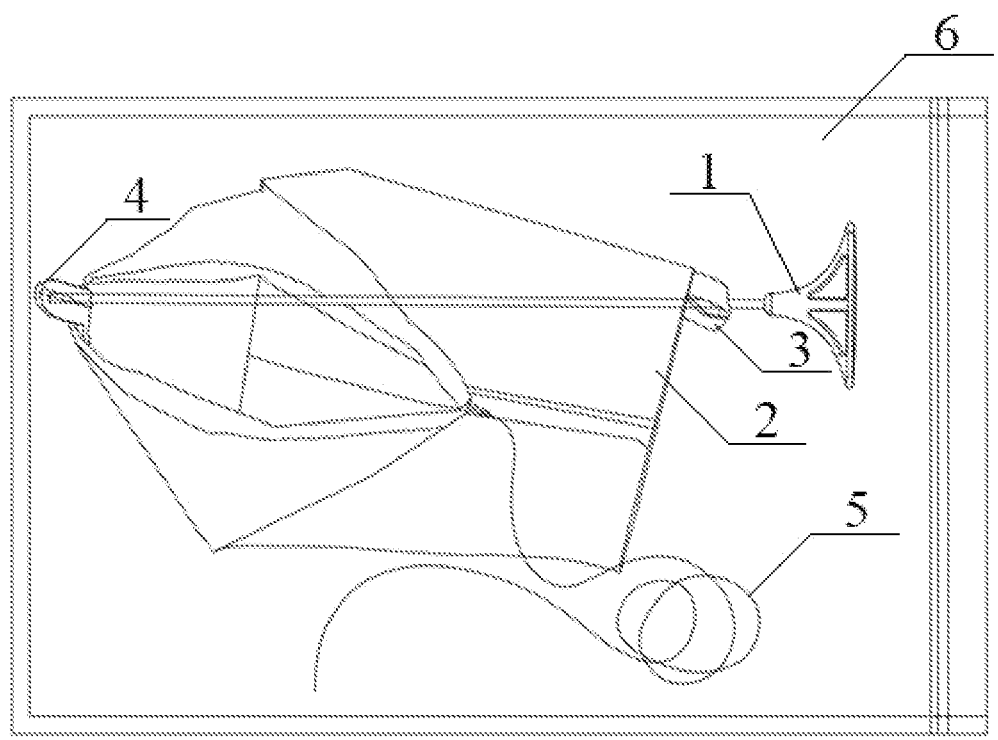
FIG. 1 is a packing schematic diagram of one kind of specimen retrieval device in accordance with an embodiment of the present application.

The technical solutions in the embodiments of the present application will be clearly and completely described below with reference to the accompanying drawings in the embodiments of the present application. Obviously, the described embodiments are only a part of the embodiments of the present application, rather than all the embodiments. In accordance with the embodiments in this application, all other embodiments obtained by those of ordinary skill in the art without making creative work shall fall within the protection scope of the present application.

It should be noted that if there are directional indications (such as up, down, left, right, front, back, etc.) involved in the embodiments of the present application, the directional indications are only used to explain a relative positional relationship or movement situation between components in a specific posture (as shown in the accompanying drawings). If the specific posture changes, the directional indication also changes accordingly.

In addition, in the description of the present application, all the terms used is for the purpose of illustration only and is not intended to limit the scope of the present application. The terms "comprising" and/or "including" are used to specify the presence of an element, step, operation and/or component, but do not preclude the presence or addition of one or more other elements, steps, operations and/or components. The terms "first," "second," and the like, may be used to describe various elements, and do not represent for an order, and do not limit to these elements. In addition, in the description of the present application, "plurality" means two or more, unless otherwise specified. These terms are only used to distinguish one element from another. These and/or other aspects will become apparent, and the description of the embodiments of the present application will be more readily understood by those of ordinary skill in the art in conjunction with the following drawings. The drawings are used to depict embodiments of the present application for illustrative purposes only. Those skilled in the art will readily appreciate from the following description that alternative embodiments of the structures and methods shown herein may be employed without departing from the principles of the present application.

In the related art, a nominal diameter of a trocar cannula used for laparoscopy is usually not more than 15 mm, and 5 mm, 10 mm and 12 mm are more common. In order to achieve a purpose of minimally invasive, the smallest possible trocar cannula is used to place a specimen retrieval bag with the largest possible capacity into a patient's body cavity. In a process of minimally invasive surgery, a method for taking out surgical specimens using a specimen bag with an operating rod is as follows: a specimen bag is delivered into a patient's body through an instrument channel by a handle of the operating rod, the tissue specimen or surgical resection is put into the retrieval bag, and the retrieval bag is taken out through the instrument channel after the bag mouth of the retrieval bag is locked through the handle wire of the operating rod. In the process of taking out the surgical specimen using a specimen retrieval bag without an operating rod, the specimen bag cannot be opened easily after entering the body cavity. An atraumatic instrument is required to bring the bag body into a patient's body through a trocar cannula, to avoid damage to the bag body by instruments during the operation, which can cause a failure of specimen retrieval. Taking the convenience of operation into account, some specimen retrieval devices without operating rods on the market are designed with an insertion cannula. The bag body is inserted into the trocar cannula after the retrieval bag has been rolled into the insertion cannula to facilitate the retrieval bag to enter the patient's body cavity, resulting in the specimen retrieval bag without operating rod being restricted by the diameters of a cannula and a trocar.

A specimen retrieval bag according to an embodiment of the present application includes: a bay body, an introducing tab arranged at an opening end of the bag body, and a bag extending tab arranged on a closed end of the bag body. The introducing tab and the bag extending tab are configured to cooperate with an insertion rod, and the insertion rod is configured to pass through the bag extending tab to insert a top end of the insertion rod into the introducing tab.

Figure 2:
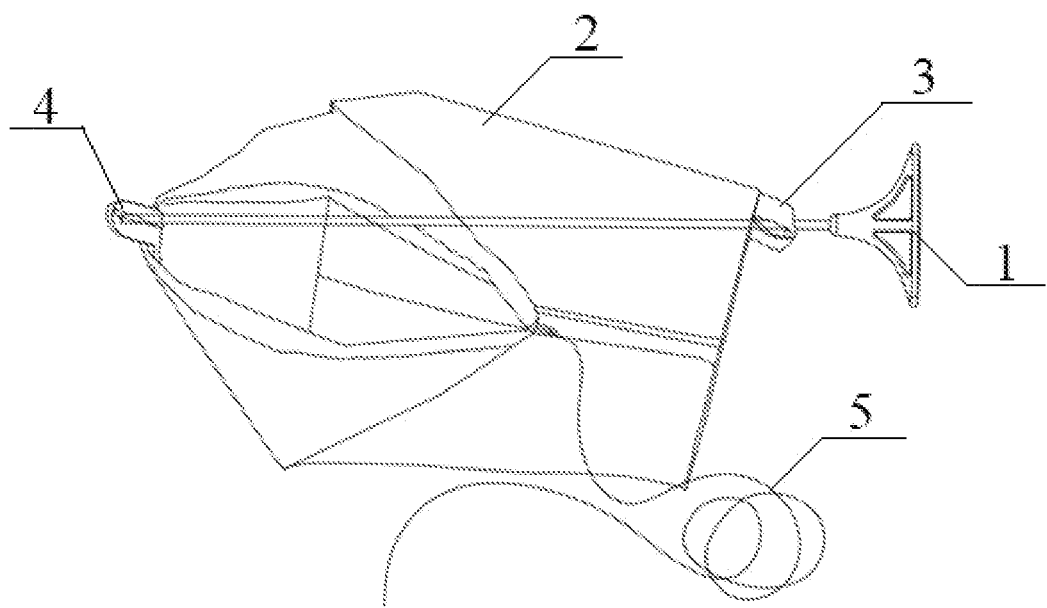
FIG. 2 is a schematic structure diagram of one kind of specimen retrieval device in accordance with an embodiment of the present application.
Figure 3:
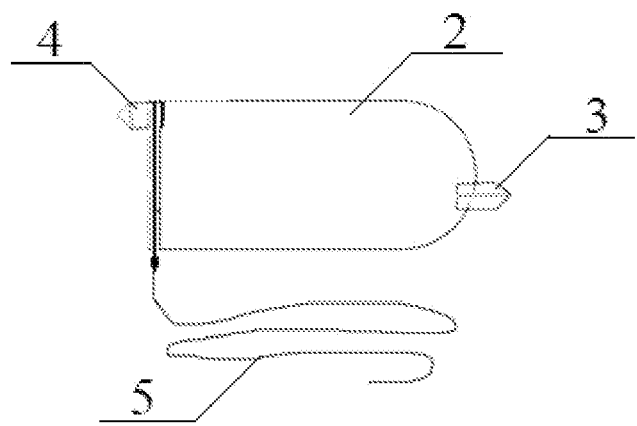
FIG. 3 is a schematic structure diagram of one kind of specimen retrieval bag in accordance with an embodiment of the present application.
Figure 4:
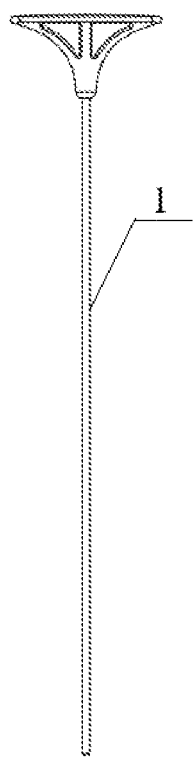
FIG. 4 is a schematic structure diagram of one kind of an insertion rod of a specimen retrieval device in accordance with an embodiment of the present application.

As shown in FIG. 2-FIG. 4, an insertion rod 1 and a bag body 2 are separated independently from each other, a bag extending tab 3 may hold and limit the insertion rod 1 to the bag body 2, and the top end of the insertion rod 1 is stably attached into an introducing tab 4. During the process of minimally invasive surgery, an operator holds an end of the insertion rod 1 and applies a pushing force to the insertion rod 1, and the bag body 2 is delivered into a patient's body through a trocar cannula under a thrust of the insertion rod 1. During the operation of the specimen retrieval bag, the bag body 2 does not need to be accommodated in the insertion rod 1, a diameter of the insertion rod 1 may be reduced to a large extent, and thus a diameter of the matching trocar cannula to be used together may be reduced, so as to achieve the purpose of minimally invasive to patients.

In an optional embodiment, the introducing tab 4 is matched with a top end of the insertion rod 1, and this may prevent the insertion rod 1 from falling out of the introducing tab 4 during the process of inserting the bag body 2 into the patient's body cavity. For example, the introducing tab 4 is set to a cone, and the top end of the insertion rod 1 is set to a cone matching with the introducing tab 4; the introducing tab 4 is set to a cylinder, and the top of the insertion rod 1 is set to a cylinder matching with the introducing tab 4. The introducing tab 4 and the top of the insertion rod 1 may also be set to other shapes, which are not specifically limited in the present application.

In an optional embodiment, an end of the insertion rod 1 is set to be tapered. That the end of the insertion rod 1 is set to be tapered is convenient for the operator to grasp the insertion rod 1, and may effectively save space and facilitate the accommodation of the insertion rod 1.

In an optional embodiment, the introducing tab 4 and the bag extending tab 3 are both provided with an X-ray developing belt. It is convenient to track the position of the bag body 2 in the patient's body cavity, and monitor in real time whether the bag body 2 is placed in a position where the surgical specimen is located.

In an optional embodiment, the specimen retrieval bag includes a closure drawstring 5, the closure drawstring 5 includes a closing section and an operating section that are connected to each other. The closing section passes through a pull ring and is provided at an opening end of the bag body 2. The operating section passes through a trocar cannula 7 and an end portion of the operation section is outside the trocar cannula 7, it is convenient to operate the closure drawstring 5 for tightening the opening end of the bag body 2. It can be understood that the closing section of the closure drawstring 5 is made of metal with good elasticity, and the operating section of the closure drawstring 5 is made of soft coarse fiber. When the bag body 2 is pushed into the trocar cannula 7, the trocar cannula 7 exerts pressure on the closing section of the closure drawstring 5 through its inner wall, and the opening end of the bag body 2 is in a flat state; when the bag body 2 is completely placed in the patient' body through the trocar cannula 7, the closing section of the closure drawstring 5 is automatically stretched and restored to its original state by its own elastic force, and the opening end of the bag body 2 is opened accordingly, which is convenient for putting tissue specimens or surgical specimens into the bag body 2. After the tissue specimen or surgical specimen is completely put into the bag body 2, the closing section of the closure drawstring 5 is compressed again into the trocar cannula 7 by tightening the operation section of the closure drawstring 5, and the operation section of the closure drawstring 5 is continuously tightened until the bag body 2 is pulled out of the patient's body cavity together with the trocar cannula 7.

In an optional embodiment, the insertion rod 1 is made of metal or hard fiber. The insertion rod 1 of this embodiment is made of high-strength metal or hard fiber material, which may ensure the strength of the insertion rod 1 whilst effectively reducing the diameter of the insertion rod 1, and a deformation or a breakage of the insertion rod 1 may be avoid during the process of pushing the bag body 2 into the patient's body cavity.

In an optional embodiment, the insertion rod 1and the bag body 2 are sealed in a packaging 6. As shown in FIG. 1, before the specimen retrieval bag is not in use, the insertion rod 1 and the bag body 2 are sealed in the packaging 6, and then the insertion rod 1, the bag body 2 and the packaging 6 are entirely put into a blister packaging and/or a medical sterilization bag, to avoid contamination of the insertion rod 1 and the bag body 2 by the external environment. A thermoplastic sealing method may be adopted to seal a bag mouth of the packaging 6. After opening the packaging, the operator may operate the specimen retrieval bag by holding the insertion rod 1 and the bag body 2 simultaneously with one hand. After the bag body 2 is taken out, the bag body 2 is folded into a triangle, and the opening end of the bag body 2 corresponds to the smallest angle of the triangle. For example, the bag body 2 may be folded into a "paper airplane"-shaped triangle, and the opening end of the bag body 2 is the smallest angle of the triangle. When the bag body 2 is pushed into the trocar cannula 7, the opening end of the bag body 2 will enter the trocar cannula 7 first, which may effectively reduce the resistance of the trocar cannula 7 to the bag body 2.

In an optional embodiment, a length of the insertion rod 1 is greater than that of the bag body 2, which is convenient to place the bag body 2 into the patient's body cavity. And the length of the insertion rod 1 should also be greater than a length of the matching trocar cannula 7.

In an optional embodiment, an outer diameter of the insertion rod 1 ranges from 1 millimeter to 3 millimeters. Preferably, the outer diameter of the insertion rod 1 is 2.5 millimeters. The insertion rod 1 and the bag body 2 are designed separately, and the bag body 2 may be placed into the patient's body cavity by a thrust of the insertion rod 1, which is no longer restricted to the trocar cannula 7 of fixed specifications, and may also choose the trocar cannula 7 with a smaller diameter to achieve minimally invasive in the true sense.

A specimen retrieval device is disclosed in this embodiment of the present application, which includes an insertion rod and the specimen retrieval bag according to any one of embodiments above, and the insertion rod and the specimen retrieval bag are designed separately.

The specific limitations of the specimen retrieval device in this embodiment may be found in the relevant descriptions of the above-mentioned embodiments, which will not be repeated here.

A method for using a specimen retrieval device is disclosed in this embodiment of the present application, a specimen retrieval device includes an insertion rod and a specimen retrieval bag, and the insertion rod and the specimen retrieval bag are separately designed. An introducing tab is arranged at an opening end of the specimen retrieval bag, and a bag extending tab is arranged on a closed end of the specimen retrieval bag. The method for using a specimen retrieval device includes the following.

S1310: inserting the specimen retrieval bag into a trocar cannula, the insertion rod is configured to pass through the bag extending tab to insert a top end of the insertion rod into the introducing tab so that the specimen retrieval bag enters the trocar cannula.

S1320: unfolding an opening end of the specimen retrieval bag and placing a specimen into the opening end of the specimen retrieval bag.

S1330: tightening the opening end of the specimen retrieval bag and taking out the specimen retrieval bag.

Figure 5:
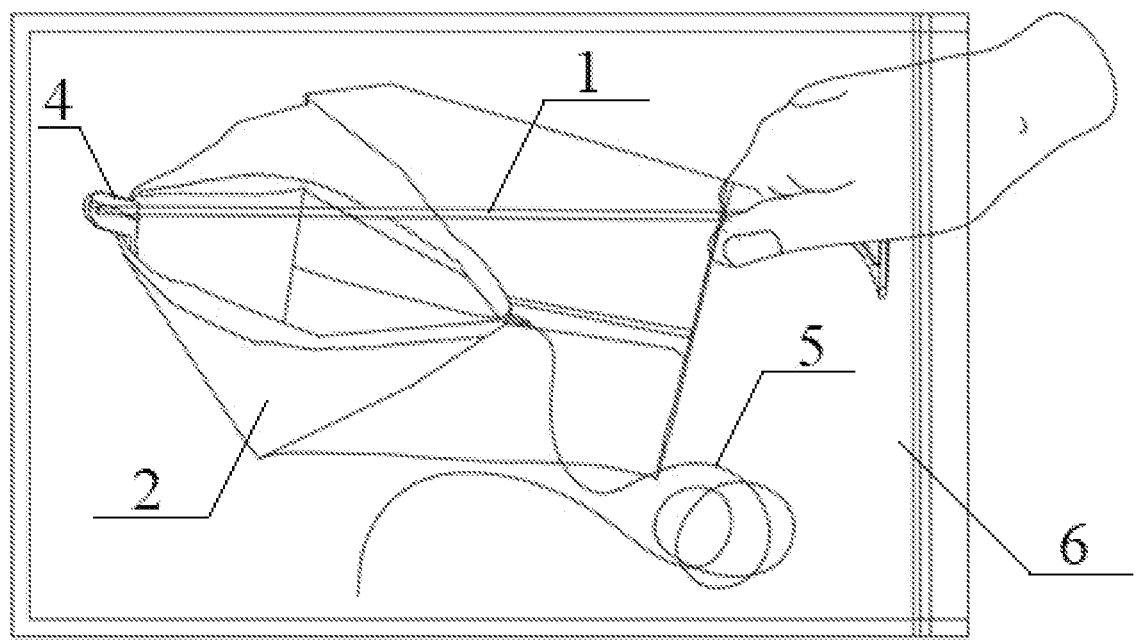
FIG. 5 is a schematic diagram of taking out a specimen retrieval device from a packaging in accordance with an embodiment of the present application.
Figure 6:
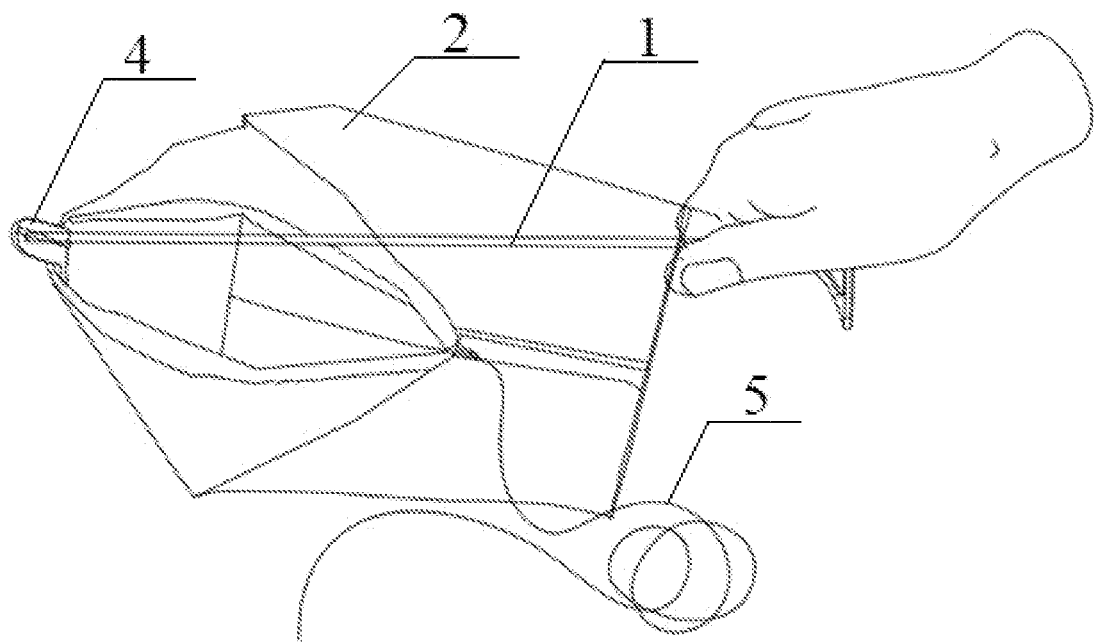
FIG. 6 is a schematic diagram of a holding state of a specimen retrieval device in accordance with an embodiment of the present application.
Figure 7:
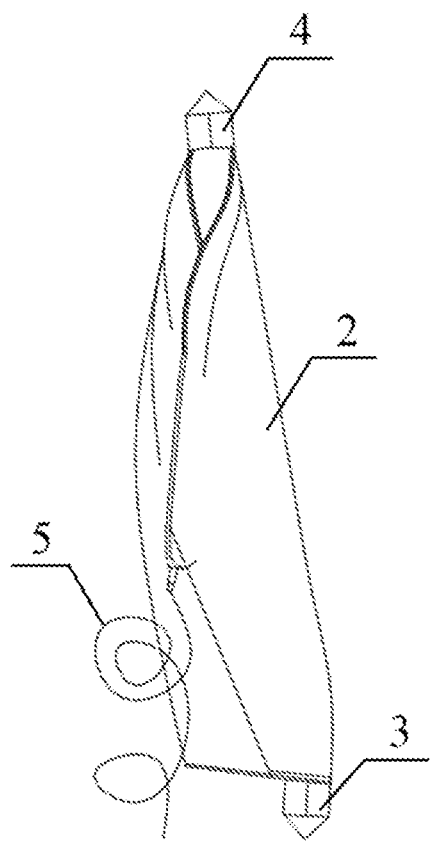
FIG. 7 is a schematic diagram of a folded state of a specimen retrieval bag before being placed in a patient's body cavity in accordance with an embodiment of the present application.
Figure 8:
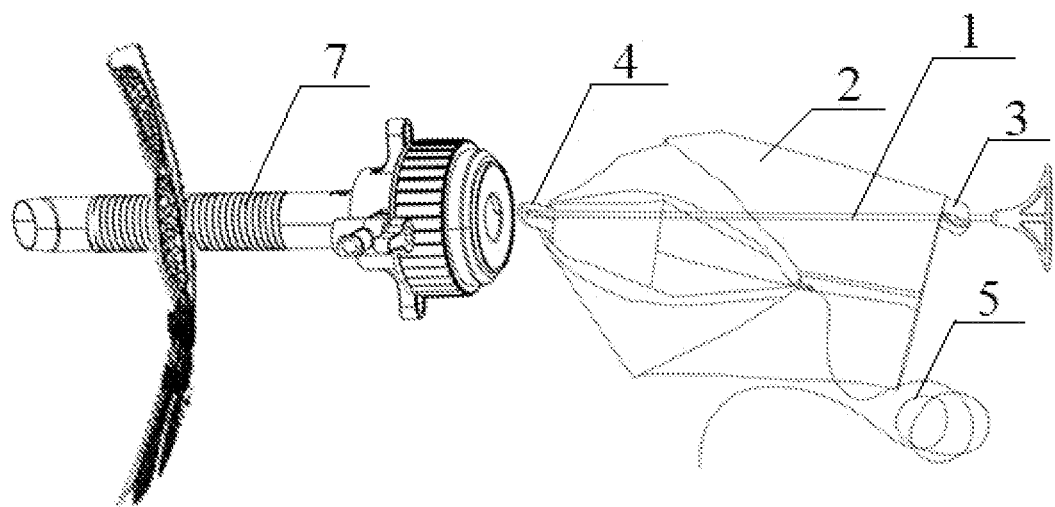
FIG. 8 is a schematic diagram of a state in which a specimen retrieval bag is placed into a trocar cannula in accordance with an embodiment of the present application.
Figure 9:
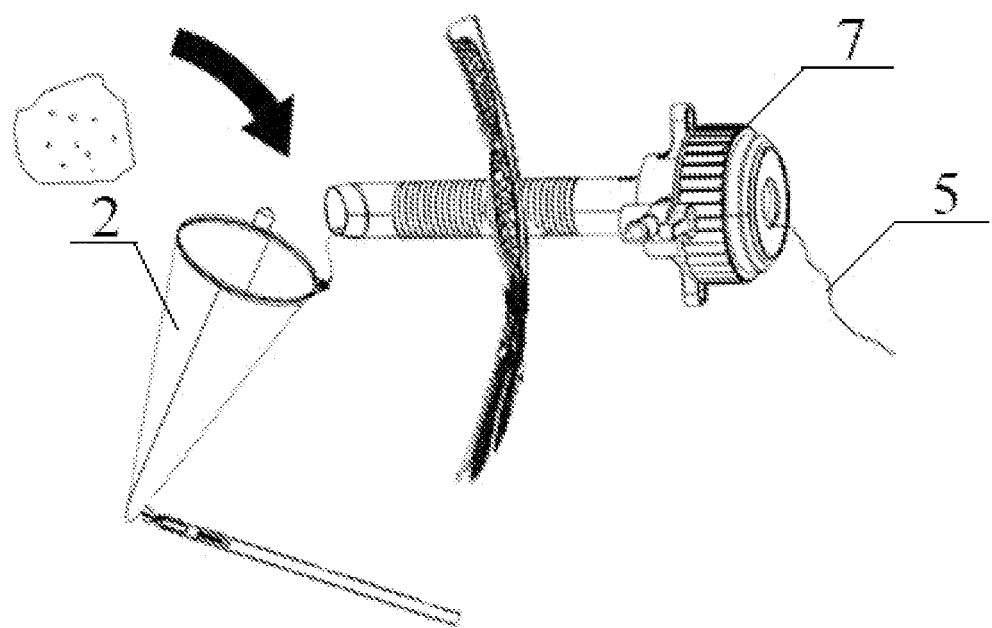
FIG. 9 is a schematic diagram of a state of placing a surgical specimen in a specimen retrieval bag in accordance with an embodiment of the present application.
Figure 10:
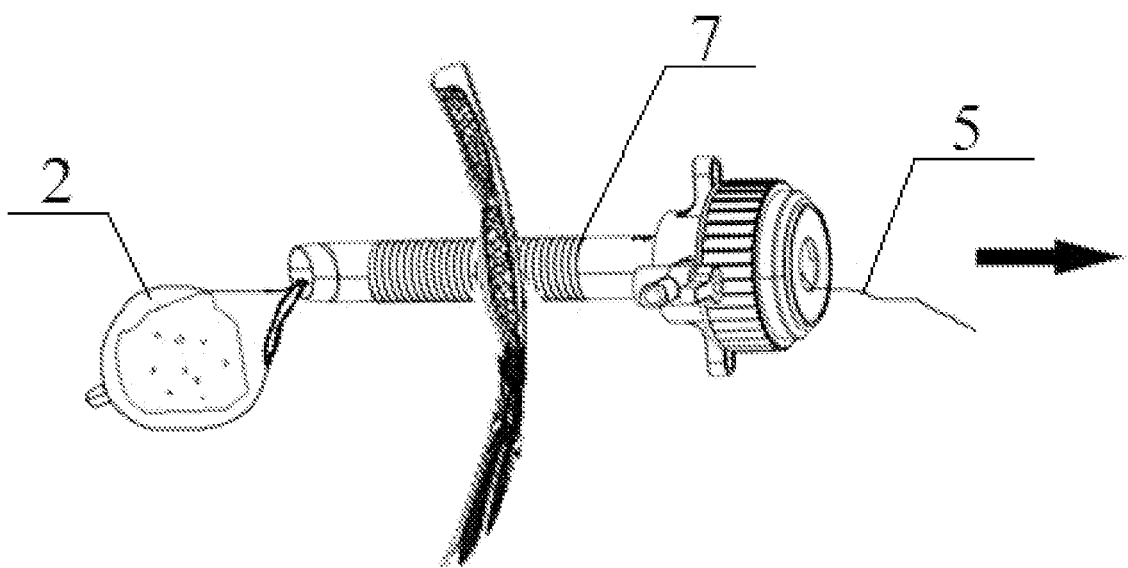
FIG. 10 is a schematic diagram of a state of placing a specimen retrieval bag containing a surgical specimen into a trocar cannula in accordance with an embodiment of the present application.
Figure 11:
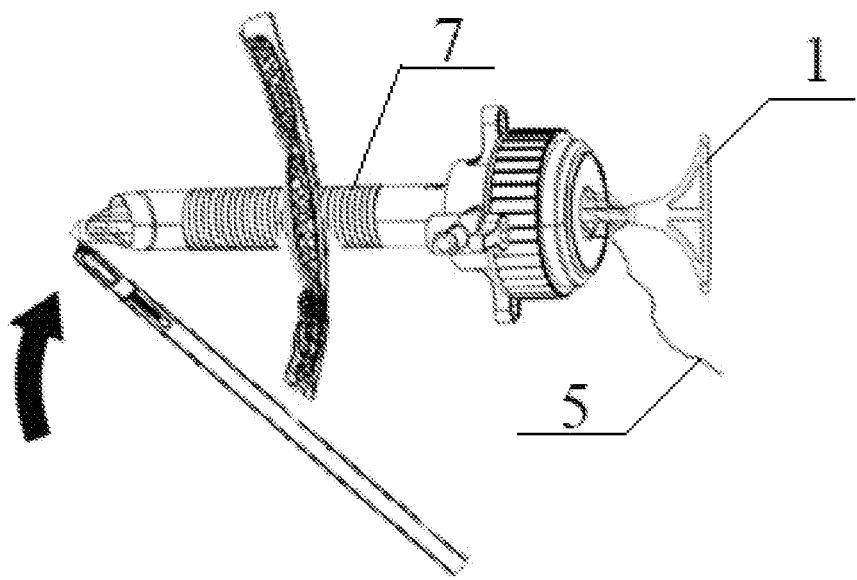
FIG. 11 is a schematic diagram of a state of taking out a specimen retrieval bag containing a surgical specimen from a trocar cannula in accordance with an embodiment of the present application.
Figure 12:
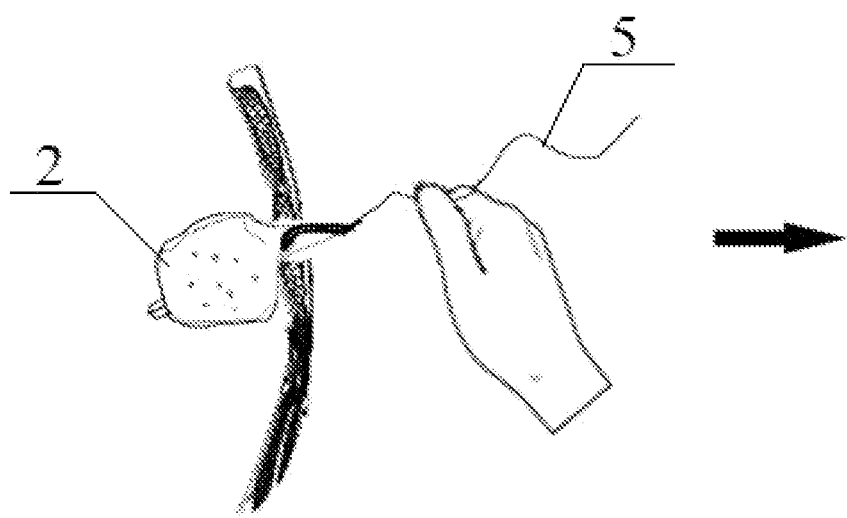
FIG. 12 is a schematic diagram of a state of taking out a specimen retrieval bag containing a surgical specimen from a patient's body cavity in accordance with an embodiment of the present application.
Figure 13:
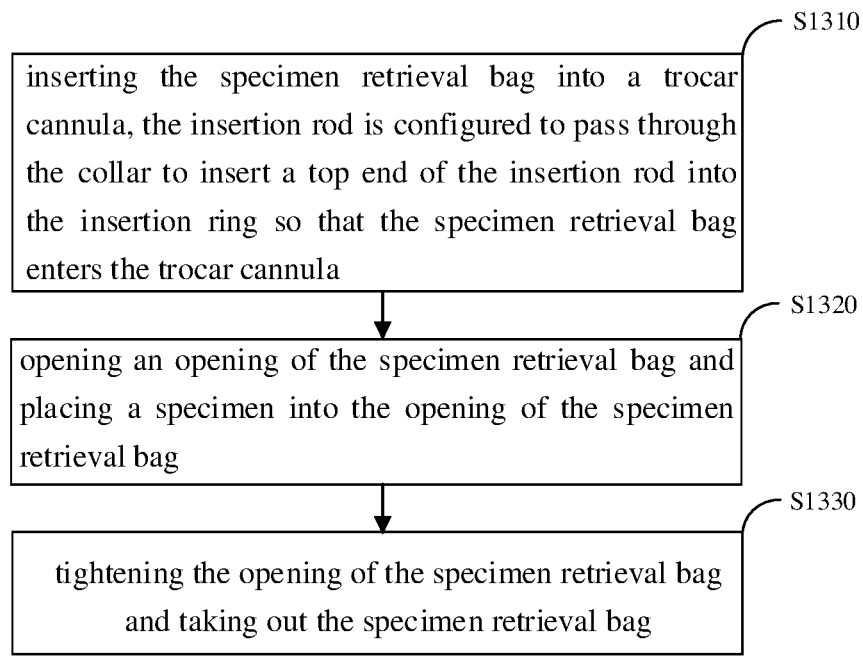
FIG. 13 is a schematic flowchart of a method for using a specimen retrieval device in accordance with an embodiment of the present application.

Specifically, a specific method of using a specimen retrieval device according to an embodiment of the present application is as follows. As shown in FIG. 5 and FIG. 6, the specimen retrieval bag is first taken out from the packaging 6, and during the process of taking it out, the operator pinches the end of the insertion rod 1 and the bag extending tab 3 to make the top end of the insertion rod 1 press against the introducing tab 4, and then the insertion rod 1 and the bag body 2 are taken out of the packaging 6; as shown in FIG. 7, before the bag body 2 is inserted into the trocar cannula 7, the bag body 2 is folded into a triangle in a manner of folding an paper airplane, which may effectively reduce a resistance of the bag body 2 when passes through the trocar cannula 7, and facilitate the bag body 2 smoothly enters the trocar cannula 7. As shown in FIG. 8, the operator pinches the insertion rod 1 and the bag extending tab 3, and pushes the bag body 2 into the trocar cannula 7 until the bag body 2 is completely inserted into the patient's body cavity. As shown in FIG. 9, after the bag body 2 enters the patient's body cavity, loosening the closure drawstring 5 and the opening end of the bag body 2 is opened, and then the surgical specimen is put into the bag body 2 by the non-invasive grasping forceps in conjunction with the endoscope. As shown in FIG. 10, after the surgical specimen is completely placed in the bag body 2, the operator tightens the opening end of the bag body 2 by tightening the closure drawstring 5 located outside the trocar cannula 7. As shown in FIG. 11, the operator pinches the insertion rod 1 and the bag extending tab 3 to take out the bag body 2 containing the surgical specimen from the patient's body cavity, and at the same time uses the non-invasive grasping forceps coordinated with endoscope to act on the closed end of the bag body 2, so that the bag body 2 containing the surgical specimen is completely inserted into the trocar cannula 7. As shown in FIG. 12, when the trocar cannula 7 is pulled out, the operator takes out the bag body 2 containing the surgical specimen from the patient's body cavity by pulling the closure drawstring 5 by hands, that is, the whole operation process of the specimen retrieval bag is complete.

In the description provided herein, numerous specific details are set forth. It should be understood, however, that the embodiments of the present application may be practiced without these specific details. In some embodiments, well-known methods, structures and techniques have not been shown in detail in order not to obscure understanding of this description.

Furthermore, it will be understood by those of ordinary skill in the art that although some of the embodiments herein include certain features, but not others, included in other embodiments, that combinations of features of different embodiments are intended to be within the scope of this application and form different embodiments. For example, in the claims, any one of the claimed embodiments may be used in any combination.

It will be understood by those skilled in the art that although the present application has been described with reference to exemplary embodiments, various changes may be made, and equivalents may be substituted for elements thereof without departing from the scope of the present application. In addition, many modifications may be made to adapt a particular situation or material to the teachings of the present application without departing from the essential scope of the present application. Therefore, the present application is not to be limited to the particular embodiments disclosed, but the present application is to include all embodiments falling within the scope of the appended claims.

What is claimed is:

1. A specimen retrieval bag, comprising:
   a bag body;
   an introducing tab arranged at an opening end of the bag body; and
   a bag extending tab arranged on a closed end of the bag body;
   wherein the introducing tab and the bag extending tab are configured to cooperate with an insertion rod, and allow the insertion rod to pass through the bag extending tab and insert a top end of the insertion rod into the introducing tab during a process of minimally invasive surgery; and
   the introducing tab and the bag extending tab are both provided with an X-ray developing belt.

2. The specimen retrieval bag according to claim 1, further comprising:
   a closure drawstring, wherein the closure drawstring comprises a closing section and an operating section that are connected to each other, the closing section is fixed to the opening end of the bag body through a pull ring, and the operating section passes through a trocar cannula and an end portion of the operating section is outside the trocar cannula.

3. The specimen retrieval bag according to claim 2, wherein the closing section is made of metal with elasticity, and the operating section is made of soft coarse fiber.

4. The specimen retrieval bag according to claim 1, wherein the introducing tab is unfolded as a cone whilst in use.

5. The specimen retrieval bag according to claim 1, wherein the introducing tab is folded as a triangular shape whilst the specimen retrieval bag is sealed in a packaging bag.

6. A specimen retrieval device, comprising:
   an insertion rod; and
   the specimen retrieval bag according to claim 1, wherein the insertion rod and the specimen retrieval bag are separately designed, wherein
   the introducing tab and the bag extending tab are both provided with an X-ray developing belt.

7. The specimen retrieval device according to claim 6, wherein the introducing tab is configured to be matched with a top end of the insertion rod.

8. The specimen retrieval device according to claim 7, wherein a shape of the top end of the insertion rod is set as one of a cone and a cylinder.

9. The specimen retrieval device according to claim 8, wherein the top end of the insertion rod is set as the cone.

10. The specimen retrieval device according to claim 9, wherein a bounding contour of a tip of the cone is shaped into an arc, and a bounding contour of an end of the cone is shaped into an arc.

11. The specimen retrieval device according to claim 6, wherein the insertion rod is made of metal or hard fiber.

12. The specimen retrieval device according to claim 6, wherein the insertion rod and the bag body are sealed in a packaging bag.

13. The specimen retrieval device according to claim 6, wherein a length of the insertion rod is greater than that of the bag body.

14. The specimen retrieval device according to of claim 6, wherein an outer diameter of the insertion rod ranges from 1 millimeter to 3 millimeters.

15. The specimen retrieval device according to claim 6, wherein the specimen retrieval bag further comprises:
   a closure drawstring, wherein the closure drawstring comprises a closing section and an operating section that are connected to each other, the closing section is fixed to the opening end of the bag body through a pull ring, and the operating section passes through a trocar cannula and an end portion of the operating section is outside the trocar cannula.

16. A method for using a specimen retrieval device, wherein, the specimen retrieval device comprises an insertion rod and a specimen retrieval bag, the insertion rod and the specimen retrieval bag are separately designed, the specimen retrieval bag comprises a bag body, an introducing tab arranged at an opening end of the bag body, a bag extending tab arranged on a closed end of the bag body, and the introducing tab and the bag extending tab are both provided with an X-ray developing belt;
the method for using a specimen retrieval device comprises:
   inserting the bag body into a trocar cannula, wherein the insertion rod is configured to pass through the bag extending tab to insert a top end of the insertion rod into the introducing tab so that the bag body enters the trocar cannula;
   unfolding an opening end of the bag body, and placing a specimen into the bag body; and
   tightening the opening end of the bag body, and taking out the bag body.

17. The method for using a specimen retrieval device according to claim 16, wherein
   the specimen retrieval bag further comprises a closure drawstring, the closure drawstring comprises a closing section and an operating section that are connected to each other, the closing section is fixed to the opening end of the bag body through a pull ring, and the operating section passes through a trocar cannula and an end portion of the operating section is outside the trocar cannula;
   the unfolding an opening end of the bag body comprises:
   loosening the closure drawstring so that the opening end of the bag body is opened; and
   the tightening the opening end of the bag body comprises:
   tightening the closure drawstring to tighten the opening end of the bag body.

18. The method for using a specimen retrieval device according to claim 16, wherein before the inserting the bag body into a trocar cannula, the method further comprises:
   folding the bag body into a triangular shape to reduce a resistance of the bag body when the bag body enters the trocar cannula.

* * * * *